United States Patent
Kim et al.

(10) Patent No.: US 9,714,211 B2
(45) Date of Patent: Jul. 25, 2017

(54) PLASTICIZER AND RESIN COMPOSITION, AND PREPARATION METHOD THEREOF

(71) Applicant: LG CHEM, LTD., Seoul (KR)

(72) Inventors: Hyun Kyu Kim, Daejeon (KR); Da Won Jung, Daejeon (KR); Mi Yeon Lee, Daejeon (KR); Dong Hyun Ko, Daejeon (KR)

(73) Assignee: LG Chem, Ltd., Seoul (KR)

( * ) Notice: Subject to any disclaimer, the term of this patent is extended or adjusted under 35 U.S.C. 154(b) by 188 days.

(21) Appl. No.: 14/412,894

(22) PCT Filed: Oct. 22, 2014

(86) PCT No.: PCT/KR2014/009979
§ 371 (c)(1),
(2) Date: Jan. 5, 2015

(87) PCT Pub. No.: WO2015/119355
PCT Pub. Date: Aug. 13, 2015

(65) Prior Publication Data
US 2016/0272780 A1 Sep. 22, 2016

(30) Foreign Application Priority Data

Feb. 7, 2014 (KR) .................. 10-2014-0014203
Feb. 24, 2014 (KR) .................. 10-2014-0021409
Oct. 22, 2014 (KR) .................. 10-2014-0143340

(51) Int. Cl.
| | |
|---|---|
| C08K 5/12 | (2006.01) |
| C07C 69/80 | (2006.01) |
| C07C 67/08 | (2006.01) |
| C07C 69/82 | (2006.01) |
| C08K 5/00 | (2006.01) |
| C07C 67/03 | (2006.01) |
| C07C 67/54 | (2006.01) |

(52) U.S. Cl.
CPC .............. *C07C 69/80* (2013.01); *C07C 67/03* (2013.01); *C07C 67/08* (2013.01); *C07C 67/54* (2013.01); *C07C 69/82* (2013.01); *C08K 5/0016* (2013.01); *C08K 5/12* (2013.01)

(58) Field of Classification Search
CPC ....................................................... C08K 5/12
See application file for complete search history.

(56) References Cited

U.S. PATENT DOCUMENTS

| | | | |
|---|---|---|---|
| 3,231,642 A * | 1/1966 | Goldman | B29C 47/0009 264/209.5 |
| 3,736,348 A | 5/1973 | Gough et al. | |
| 4,929,749 A | 5/1990 | Gupta et al. | |
| 7,371,799 B2 | 5/2008 | Mather et al. | |
| 2010/0305250 A1 * | 12/2010 | Colle | C08K 5/0016 524/112 |

FOREIGN PATENT DOCUMENTS

| | | |
|---|---|---|
| CN | 1611482 A | 5/2005 |
| CN | 101679708 A | 3/2010 |
| CN | 102516080 A | 6/2012 |
| CN | 102876275 A | 1/2013 |
| GB | 851753 A | 10/1960 |
| JP | 07-157614 A | 6/1995 |
| JP | 10029870 A | 2/1998 |
| JP | 2009-269939 A | 11/2009 |
| JP | 2012089287 | 5/2012 |
| JP | 2012092074 | 5/2012 |
| JP | 2012255104 | 12/2012 |
| KR | 1020060087889 | 8/2006 |
| KR | 100812511 B1 | 3/2008 |
| KR | 1020090047570 A | 5/2009 |
| KR | 20110012333 | 2/2011 |
| KR | 10-2013-0035493 A | 4/2013 |
| KR | 1020140126648 A | 10/2014 |

OTHER PUBLICATIONS

Shou, et al.: "The Synthesis of a Low-Cost Plasticizer DOTP/DOIP for PVC Plastic Products", Engineering Plastics Application, vol. 25, No. 3, Jun. 15, 1997, pp. 25-27.
Jia Changying: "Producing mixed plasticizer from TA residue", Guangxi Chemical Industry, vol. 28, No. 1, Mar. 10, 1999, pp. 54-56.
Qi Yanwei: "Synthesis of a mixed plasticizer from terephthalic acid residue", China Master's Theses Full-Text Database (electronic periodical) Engineering I, Dec. 31, 1996, pp. 29-50.

* cited by examiner

*Primary Examiner* — Robert Harlan
(74) *Attorney, Agent, or Firm* — Dentons US LLP

(57) ABSTRACT

Provided are a plasticizer and a resin composition including the plasticizer, and a method of preparing the same. The plasticizer may improve physical properties, such as light resistance required for a compound formulation or viscosity, bleeding phenomenon, and gelling property required for a sheet formulation, when used as a plasticizer of a resin composition, by improving poor physical properties that have been ascribed to structural limitations although having environmental friendliness.

17 Claims, No Drawings

PLASTICIZER AND RESIN COMPOSITION, AND PREPARATION METHOD THEREOF

This application is a National Stage Entry of International Application No. PCT/KR2014/009979, filed Oct. 22, 2014, and claims the benefit of Korean Application Nos. 10-2014-0014203, filed on Feb. 7, 2014, 10-2014-0021409, filed Feb. 24, 2014, and 10-2014-0143340, filed on Oct. 22, 2014, all of which are hereby incorporated by reference in their entirety for all purposes as if fully set forth herein.

TECHNICAL FIELD

The present invention relates to a plasticizer and a resin composition, and a preparation method thereof, and more particularly, to a plasticizer and a resin composition which may improve poor physical properties that have been ascribed to structural limitations although having environmental friendliness, and a method of preparing the plasticizer and the resin composition.

BACKGROUND ART

Typically, with respect to a plasticizer, alcohol reacts with polycarboxylic acid, such as phthalic acid and adipic acid, to form an ester corresponding thereto. Also, in consideration of domestic and foreign regulations limiting phthalate-based plasticizers that are harmful to human body, research into environmentally friendly plasticizers, which may replace phthalate-based plasticizers such as terephthalate-based plasticizers, adipate-based plasticizer, and other polymer-based plasticizers, has continued.

In order to manufacture flooring materials, wallpaper, sheet products which require light resistance as a physical property, an appropriate plasticizer must be used in consideration of discoloration. With respect to a polyvinyl chloride (PVC) based compound formulation for a wall paper or sheet, additives such as plasticizers, fillers, stabilizers, viscosity reducing agents, dispersants, antifoaming agents, and a foaming agents are mixed with a PVC resin according to properties required by the corresponding standards, such as tensile strength, elongation rate, light resistance, bleeding phenomenon, and gelling property.

For example, in the case that inexpensive dioctyl terephthalate is used among environmentally friendly plasticizers that are applicable to PVC, since its viscosity is high and the absorption rate of the plasticizer is relatively low, a bleeding phenomenon, in which the plasticizer comes out from the backside of a sheet, is not only observed, but gelling property is also not excellent.

Thus, there is a continuous need to research into techniques by which a product better than the dioctyl terephthalate or a novel composition including dioctyl terephthalate is developed and optimally used as a plasticizer for a vinyl chloride-based resin.

PRIOR ART DOCUMENTS

Patent Documents (Patent Document 1) Korean Patent Application Laid-Open Publication No. 2006-0087889 (Mar. 8, 2006)

DISCLOSURE OF THE INVENTION

Technical Problem

As a result of continuous research into plasticizers, the present inventors found an environmentally friendly plasticizer which may improve poor physical properties that have been ascribed to structural limitations although having environmental friendliness, thereby leading to the completion of the present invention.

The present invention provides a plasticizer which may improve physical properties, such as light resistance required for a compound formulation when used as a plasticizer of a resin composition, or viscosity, bleeding phenomenon, and gelling property required for a sheet formulation, a preparation method thereof, and a resin composition including the plasticizer.

Technical Solution

According to an aspect of the present invention, there is provided a plasticizer including isophthalate and terephthalate. According to another aspect of the present invention, there is provided a method of preparing a plasticizer including:

adding both isophthalic acid and terephthalic acid to alcohol to obtain a mixture;

adding a catalyst to the mixture to react in a nitrogen atmosphere;

removing unreacted alcohol and neutralizing unreacted acid; and dehydrating and filtering by vacuum distillation to obtain a plasticizer.

According to another aspect of the present invention, there is provided a method of preparing a plasticizer including: preparing an ester-based mixture including terephthalate and isophthalate; and obtaining a plasticizer by blending the terephthalate and the isophthalate to include the isophthalate in an amount of 1 wt % to 99 wt % based on a total weight of the ester-based mixture.

According to another aspect of the present invention, there is provided a resin composition including the plasticizer in an amount of 5 parts by weight to 150 parts by weight based on 100 parts by weight of a resin selected from the group consisting of ethylene vinyl acetate, polyethylene, polypropylene, polyvinyl chloride, polystyrene, polyurethane, and a thermoplastic elastomer.

Advantageous Effects

According to the present invention, a plasticizer, which may improve physical properties, such as light resistance required for a compound formulation when used as a plasticizer of a resin composition, or viscosity, bleeding phenomenon, and gelling property required for a sheet formulation, by improving poor physical properties that have been ascribed to structural limitations although having environmental friendliness, and a resin composition including the plasticizer may be provided.

MODE FOR CARRYING OUT THE INVENTION

Hereinafter, the present invention will be described in detail.

First, the present invention has technical features that provide a plasticizer which may improve poor physical properties that have been ascribed to structural limitations although having environmental friendliness.

According to an embodiment of the present invention, a plasticizer including isophthalate and terephthalate is provided.

The plasticizer according to the present invention is an environmentally friendly plasticizer, wherein the expression "environmentally friendly plasticizer" may denote an ether-free ester-based plasticizer or ether-free phthal-type ester-based plasticizer, unless otherwise specified. Herein, the phthalate may include both isophthalate and terephthalate.

The expression "ester-free" denotes that an amount of an ether component included in the plasticizer is in a range of 1,000 ppm or less, 100 ppm or less, or 10 ppm or less.

In the plasticizer according to the embodiment of the present invention, a mixing ratio of the isophthalate to the terephthalate may be in a range of 1:99 to 99:1 as a weight ratio.

In the plasticizer according to the embodiment of the present invention, the mixing ratio of the isophthalate to the terephthalate may be in a range of 20:80 to 99:1, 50:50 to 99:1, or 50:50 to 90:10 as a weight ratio.

Also, in the plasticizer according to the embodiment of the present invention, the mixing ratio of the isophthalate to the terephthalate may be in a range of 60:40 to 90:10 as a weight ratio.

In the plasticizer according to the embodiment of the present invention, the isophthalate may be included in an amount of 1 wt % to 99 wt %, 20 wt % to 99 wt %, 50 wt % to 99 wt %, 50 wt % to 90 wt %, or 60 wt % to 90 wt % based on a total weight of the plasticizer.

Specifically, in the plasticizer according to the embodiment of the present invention, the amount of the isophthalate may be the same as or greater than an amount of the terephthalate.

In the plasticizer according to the embodiment of the present invention, when the amount of the isophthalate used is the same as or greater than the amount of the terephthalate, hardness and elongation rate may be significantly improved during the preparation of a compound formulation or sheet formulation, and thus, productivity and workability of the product may be improved and an effect of increasing plasticizing efficiency may be excellent.

The isophthalate, for example, may have an end group independently selected from alkyl groups having 1 to 12 carbon atoms, 3 to 11 carbon atoms, 4 to 10 carbon atoms, 8 to 10 carbon atoms, 8 and 9 carbon atoms, or 8 carbon atoms.

In particular, in the plasticizer according to the embodiment of the present invention, since the isophthalate includes an end group selected from alkyl groups having 8 to 10 carbon atoms, migration resistance and heating loss may be significantly improved in comparison to a plasticizer using an ester having an end group selected from alkyl groups having 7 or less carbon atoms. In the case that migration resistance and heating loss are increased, it may be very detrimental to processability and long-term stability of the final product. In particular, an increase in heating loss may mean a decrease in the amount of the plasticizer present in the final product.

Thus, the plasticizer according to the embodiment of the present invention may include the isophthalate which includes an ester having an end group selected from alkyl groups having 8 to 10 carbon atoms in order to improve migration resistance and heating loss.

In the plasticizer according to the embodiment of the present invention, the isophthalate may be dialkylisophthalate, and the alkyl may be an alkyl having 1 to 12 carbon atoms, 3 to 11 carbon atoms, 4 to 10 carbon atoms, 8 to 10 carbon atoms, 8 and 9 carbon atoms, or 8 carbon atoms.

As a specific example, the isophthalate may have a structure represented by Chemical Formula 1 below.

[Chemical Formula 1]

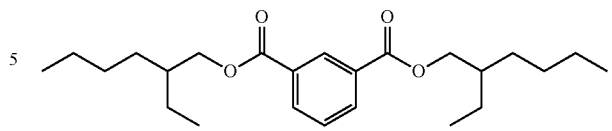

Also, according to the plasticizer according to the embodiment of the present invention, the terephthalate may be included in an amount of 1 wt % to 99 wt %, 1 wt % to 80 wt %, 1 wt % to 50 wt %, 10 wt % to 50 wt %, or 10 wt % to 40 wt % based on the total weight of the plasticizer.

The terephthalate may have an end group independently selected from alkyl groups having 1 to 12 carbon atoms, 3 to 11 carbon atoms, 4 to 10 carbon atoms, 8 to 10 carbon atoms, 8 and 9 carbon atoms, or 8 carbon atoms.

As a specific example, the terephthalate may include an alkyl group having the same number of carbon atoms as the end group of the above-described isophthalate.

According to an embodiment of the present invention, since the terephthalate particularly includes an end group selected from alkyl groups having 8 to 10 carbon atoms, migration resistance and heating loss may be significantly improved in comparison to a plasticizer using an ester having an end group selected from alkyl groups having 7 or less carbon atoms. In the case that migration resistance and heating loss are increased, it may be very detrimental to processability and long-term stability of the final product. In particular, an increase in heating loss may mean a decrease in the amount of the plasticizer present in the final product.

Thus, the plasticizer according to the embodiment of the present invention may include the terephthalate which includes an ester having an end group selected from alkyl groups having 8 to 10 carbon atoms in order to improve migration resistance and heating loss.

In the plasticizer according to the embodiment of the present invention, the terephthalate may be dialkylterephthalate, and the alkyl may be an alkyl having 1 to 12 carbon atoms, 3 to 11 carbon atoms, 4 to 10 carbon atoms, 8 to 10 carbon atoms, 8 and 9 carbon atoms, or 8 carbon atoms.

As another example, the terephthalate may have a structure represented by Chemical Formula 2 below.

[Chemical Formula 2]

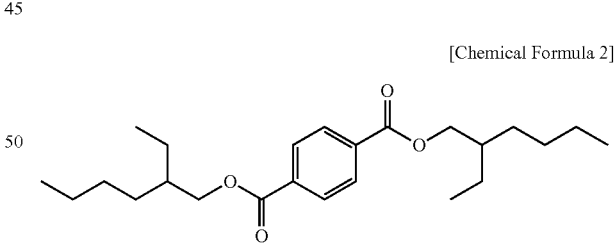

A one-pot preparation method or a blending method may be used as a method of preparing the plasticizer according to the embodiment of the present invention. For example, the one-pot preparation method is as follows:

That is, isophthalic acid is added to alcohol (hereinafter, referred to as "first step").

A catalyst is added to the mixture and reacted in a nitrogen atmosphere.

Thereafter, unreacted alcohol is removed and unreacted acid is neutralized.

Subsequently, dehydration and filtration may be performed by vacuum distillation to prepare the plasticizer.

As a specific example, the isophthalic acid and the terephthalic acid may be added in a weight ratio of 20:80 to 99:1, 50:50 to 99:1, or 50:50 to 90:10.

Also, as another example, the isophthalic acid and the terephthalic acid may be added in a weight ratio of 60:40 to 90:10.

Also, for example, the blending method is as follows:

Terephthalate and isophthalate are prepared.

The plasticizer may be prepared by blending the terephthalate and the isophthalate so as to include the isophthalate in an amount of 1 wt % to 99 wt %, 20 wt % to 99 wt %, 50 wt % to 99 wt %, 50 wt % to 90 wt %, or 60 wt % to 90 wt %.

In the blending method, the terephthalate may be prepared by the steps of: adding terephthalic acid to alcohol and then adding a catalyst to react in a nitrogen atmosphere; removing unreacted alcohol and neutralizing unreacted acid; and dehydrating and filtering by vacuum distillation.

Also, in the blending method, the isophthalate may be prepared by the steps of: adding isophthalic acid to alcohol and then adding a catalyst to react in a nitrogen atmosphere; removing unreacted alcohol and neutralizing unreacted acid; and dehydrating and filtering by vacuum distillation.

The alcohol used in the one-pot preparation method or blending method, for example, may be an aliphatic or aromatic compound having an alkyl group having 1 to 20 carbon atoms. Specific examples of the alcohol may be at least one selected from the group consisting of aliphatic alcohols having an alkyl group having 1 to 20 carbon atoms and isomers thereof, such as methanol, ethanol, propanol, n-butanol, iso-butanol, tert-butanol, pentanol and isomers thereof, hexanol and isomers thereof, heptanol and isomers thereof, octanol and isomers thereof such as 2-ethylhexyl alcohol and n-octyl alcohol, nonanol and isomers thereof such as isononyl alcohol, decanol and isomers thereof such as 2-propylheptyl alcohol, 4-methyl-2-propyl hexyl alcohol, 5-methyl-2-propyl-hexyl alcohol, n-decyl alcohol, undecanol and isomers thereof, and dodecanol and isomers thereof, and aromatic alcohols having an alkyl group having 1 to 20 carbon atoms or not, such as phenol and benzyl alcohol.

As another example, the alcohol may be a branched-chain aliphatic alcohol having an alkyl group having 1 to 20 carbon atoms, 1 to 12 carbon atoms, 3 to 11 carbon atoms, 4 to 10 carbon atoms, 8 to 10 carbon atoms, 8 and 9 carbon atoms, or 8 carbon atoms.

The alcohol used in the one-pot preparation method may be used in an amount of 150 mol % to 500 mol %, 200 mol % to 400 mol %, 200 mol % to 350 mol %, 250 mol % to 400 mol %, or 270 mol % to 330 mol % based on total 100 mol % of a mixture of the terephthalic acid and the isophthalic acid.

Also, the alcohol used in the blending method may be used in an amount of 150 mol % to 500 mol %, 200 mol % to 400 mol %, 200 mol % to 350 mol %, 250 mol % to 400 mol %, or 270 mol % to 330 mol % based on 100 mol % of the terephthalic acid.

Furthermore, the alcohol used in the blending method may be used in an amount of 150 mol % to 500 mol %, 200 mol % to 400 mol %, 200 mol % to 350 mol %, 250 mol % to 400 mol %, or 270 mol % to 330 mol % based on 100 mol % of the isophthalic acid.

Examples of the catalyst used in the one-pot preparation method or the blending method may include at least one selected from the group consisting of acid catalysts such as sulfuric acid, hydrochloric acid, nitric acid, para-toluenesulfonic acid, methanesulfonic acid, ethanesulfonic acid, propanesulfonic acid, butanesulfonic acid, and alkyl sulfuric acid; metal salts such as aluminum lactate, lithium fluoride, potassium chloride, cesium chloride, calcium chloride, ferric chloride, and aluminum phosphate; metal oxide such as heteropolyacid; natural/synthetic zeolite; cation and anion exchange resins; and organic metals such as tetra alkyl titanate and polymers thereof. As a specific example, tetra alkyl titanate may be used.

An amount of the catalyst used may vary depending on the type thereof, and for example, with respect to a uniform catalyst, the amount of the catalyst used may be in a range of 0.01 wt % to 5 wt %, 0.01 wt % to 3 wt %, 1 wt % to 5 wt %, or 2 wt % to 4 wt % based on total 100 wt % of a reactant. With respect to a non-uniform catalyst, the amount of the catalyst used may be in a range of 5 wt % to 200 wt %, 5 wt % to 100 wt %, 20 wt % to 200 wt %, or 20 wt % to 150 wt % based on the total weight of the reactant.

In this case, the reaction temperature may be in a range of 180° C. to 280° C., 200° C. to 250° C., or 210° C. to 230° C.

The plasticizer thus prepared may provide a resin composition that is effective to both compound formulation and sheet formulation by being included in an amount of 5 parts by weight to 150 parts by weight, 40 parts by weight to 100 parts by weight, or 40 parts by weight to 50 parts by weight based on 100 parts by weight of a resin selected from the group consisting of ethylene vinyl acetate, polyethylene, polypropylene, polyvinyl chloride, polystyrene, polyurethane, and a thermoplastic elastomer.

For example, the resin composition may be used in manufacturing electric wires, flooring materials, automotive interior materials, films, sheets, wallpaper, or tubes.

Hereinafter, the present invention will be described in detail, according to specific examples. However, the following examples are merely presented to exemplify the present invention, and the scope of the present invention is not limited thereto.

Preparation Example 1: One-Pot Preparation 1

1.8 g of tetraisopropyl titanate as a reaction catalyst was added to a reactant, in which 1.5 mol terephthalic acid, 1.5 mol isophthalic acid, and 9.0 mol 2-ethylhexanol were mixed in a five-neck round flask equipped with a temperature sensor, a mechanical stirrer, a condenser, a decanter, and a nitrogen injection apparatus, and the reaction was performed for 5 hours while increasing temperature to 220° C.

After the reaction, an excessive amount of alcohol was extracted under reduced pressure, and neutralization and washing processes were performed using soda ash and distilled water. Then, dehydration and filtration were carried out by vacuum distillation.

As a result of analyzing the obtained composition with a GC-Mass analyzer, it was identified that the composition was formed of compounds respectively having the following Chemical Formulae 1 and 2 and a weight ratio was 50:50.

[Chemical Formula 1]

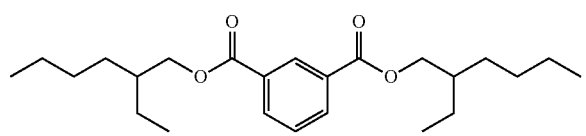

-continued

[Chemical Formula 2]

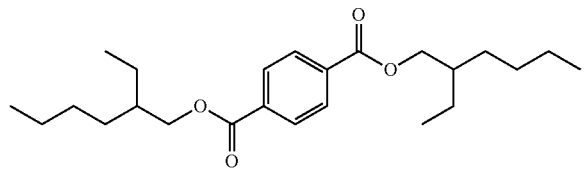

Preparation Example 2: One-Pot Preparation 2

The same process was repeated except that a reactant, in which 2.1 mol terephthalic acid, 0.9 mol isophthalic acid, and 9.0 mol 2-ethylhexanol were mixed, was used in Preparation Example 1.

As a result of analyzing the obtained plasticizer with a GC-Mass analyzer, it was identified that the plasticizer included the compounds respectively having Chemical Formulae 2 and 1, which were suggested in Preparation Example 1, at a weight ratio of 70:30 (Chemical Formula 2:Chemical Formula 1).

Preparation Example 3: One-Pot Preparation 3

The same process was repeated except that a reactant, in which 3.0 mol isophthalic acid and 9.0 mol 2-ethylhexanol were mixed while not using terephthalic acid, was used in Preparation Example 1.

As a result of analyzing the obtained plasticizer with a GC-Mass analyzer, it was identified that the plasticizer was a compound having Chemical Formula 1 which was suggested in Preparation Example 1.

Preparation Example 4: Blending Preparation 1

The same process was repeated except that a reactant, in which 3.0 mol terephthalic acid and 9.0 mol 2-ethylhexanol were mixed while not using isophthalic acid, was used in Preparation Example 1.

As a result of analyzing the obtained plasticizer with a GC-Mass analyzer, it was identified that the plasticizer was a compound having Chemical Formula 2 which was suggested in Preparation Example 1.

The compound thus obtained and the compound obtained in Preparation Example 3 were mixed in a weight ratio of 70:30 (Chemical Formula 2:Chemical Formula 1).

Preparation Example 5: Blending Preparation 2

The compound obtained in Preparation Example 4 and the compound obtained in Preparation Example 3 were mixed in a weight ratio of 50:50.

<Compound Formulation>

The plasticizers obtained in preparation Examples 1 to 5 were respectively used as experimental samples of Example 1 to 4 and Comparative Example 3.

Also, the following products were respectively prepared as experimental samples of Comparative Examples 1 and 2.

Dioctyl phthalate (DOP): LGflex DOP by LG Chem Ltd.
Dioctyl terephthalate (DOTP): GL300 by LG Chem Ltd.

The samples of Examples 1 to 4 and Comparative Example 3 using the plasticizers obtained in Preparation Examples 1 to 5 and the samples of Comparative Examples 1 and 2 using commercial plasticizers were prepared in accordance with ASTM D638 and in such a manner that 50 parts by weight of a plasticizer, 40 parts by weight of a filler, 5 parts by weight of a stabilizer, and 0.3 pats by weight of stearic acid were mixed with 100 parts by weight of PVC at a temperature of 100° C. at 500 rpm for 2 minutes and at 1,300 rpm for about 10 minutes in a 3 L super mixer. Then, roll milling was performed at 170° C. for 4 minutes to prepare 5 mm thick sheets. After pressing was performed at 185° C. while being subjected to preheating for 3 minutes, heating for 3 minutes, and cooling for 3 minutes, 1 to 3 mm thick sheets were prepared to prepare several dumbbell-shaped samples as type "C" samples.

Each sample was subjected to the following physical tests, and the results thereof are presented in Table 1 below.

<Test Items>

Presence of Bleeding and Accelerated Weathering (QUV):

After irradiating the samples with ultraviolet (UV) rays at a QUV oven temperature of 100° C. for 200 hours, the samples were taken out from the oven, and the presence of bleeding was checked and ΔE was measured using a colorimeter.

Hardness (ASTMD785):

A hardness-tester ("C" type) stylus was fully lowered down and a hardness value appeared after 10 seconds was then recorded. Tests were performed on 3 positions for each sample, and the average hardness value was then calculated.

Tensile Strength and Elongation Rate (ASTM D638):

Elongation rate and tensile strength at a breaking point of each sample were measured after pulling the sample at a cross-head speed of 200 mm/min using a test instrument, U.T.M. The tensile strength was calculated by the equation: tensile strength $(kgf/cm^2)$=load (kgf)/(thickness (cm)×width (cm)), and the elongation rate was calculated by the equation: elongation rate (%)=extension/initial length×100.

TABLE 1

| Item | | Example 1 | Example 2 | Comparative Example 3 | Example 3 | Example 4 | Comparative Example 1 | Comparative Example 2 |
|---|---|---|---|---|---|---|---|---|
| Preparation Example No. | | 1 | 2 | 3 | 4 | 5 | — | — |
| Physical Presence of bleeding | | absence | absence | absence | absence | absence | absence | presence |
| QUV (ΔE) | | 1.86 | 2.18 | 1.02 | 2.10 | 1.75 | 1.01 | 3.29 |
| Hardness | | 88.5 | 90.0 | 88.0 | 89.8 | 88.7 | 88.0 | 90.7 |
| Room temperature | Elongation rate (%) | 259.2 | 257.9 | 263.1 | 257.5 | 260.2 | 262.5 | 252.1 |
| | Tensile strength $(kg/cm^2)$ | 184.5 | 185.4 | 180.5 | 185.0 | 184.0 | 180.7 | 190.8 |

As illustrated in Table 1, the performance of Examples 1 to 4 were the same as or better than the performance of Comparative Example 1, and Examples 1 to 4 showed improvements in all items, such as bleeding phenomenon, light resistance, and tensile strength, in comparison to the DOTP product of Comparative Example 2.

With respect to the tensile strength, it may be understood that tensile strengths of Examples 1 to 4, in which the isophthalate and the terephthalate were mixed, were improved by 5% or more in comparison to that of Comparative Example 3 using only the isophthalate.

temperature bath for 4 hours or more. Thereafter, a sample weight (Wq) was measured and migration loss was calculated by the equation: $(W_i-W_q)/W_i \times 100$.

Heating Loss:

An initial weight (Wi) of each sample was measured to 4 decimal places. The sample was fixed with a clamp in an 80° C. oven, and the sample was taken out from the oven after 72 hours and stored in a constant temperature bath for 4 hours or more. Then, a sample weight (Wo) was measured and heating loss was calculated by the equation: $(W_i-W_o)/W_i \times 100$.

TABLE 2

| Category | | Example 1 | Example 2 | Comparative Example 3 | Example 3 | Example 4 | Comparative Example 1 | Comparative Example 2 |
|---|---|---|---|---|---|---|---|---|
| Preparation | Example No. | 1 | 2 | 3 | 4 | 5 | — | — |
| Physical properties | Hardness | 82.0 | 82.5 | 80.0 | 82.3 | 81.8 | 80.2 | 83.5 |
| | Tensile strength (kg/cm$^2$) | 193.0 | 195.8 | 184.9 | 195.0 | 192.7 | 185.3 | 196.8 |
| | Elongation rate (%) | 360.2 | 357.1 | 364.2 | 356.8 | 358.5 | 365.8 | 352.1 |
| | Migration resistance (%) | 9.9 | 9.7 | 10.0 | 9.7 | 9.8 | 10.1 | 9.4 |
| | Heating loss (%) | 1.5 | 1.4 | 1.5 | 1.5 | 1.5 | 4.6 | 1.3 |

Also, it may be confirmed that all of the ester-based plasticizers of Examples 1 to 4 had an amount of ether of 1,000 ppm or less which was measured using a gas chromatograph system by Agilent Technologies (Agilent 7890 GC, column: HP-5, carrier gas: helium).

<Sheet Formulation>

The samples using the plasticizers obtained in Preparation Examples 1 to 5 and the samples of Comparative Examples 1 and 2 using commercial plasticizers were prepared in accordance with ASTM D638 and in such a manner that 80 parts by weight of a plasticizer, 2 parts by weight of epoxidized soybean oil (ESO) as a second plasticizer, and 2 parts by weight of a barium-zinc stabilizer were mixed with 100 parts by weight of PVC at a temperature of 100° C. at 500 rpm for 2 minutes and at 1,300 rpm for about 10 minutes in a 3 L super mixer. Then, roll milling was performed at 160° C. for 3 minutes to prepare 5 mm thick sheets.

After pressing was performed at 185° C. while being subjected to preheating for 3 minutes, heating for 3 minutes, and cooling for 3 minutes, 1 to 3 mm thick sheets were prepared to prepare several dumbbell-shaped samples as type "C" samples.

Each sample was subjected to the following physical tests, and the results thereof are presented in Table 2 below.
<Test Items>
Hardness (ASTMD785), Tensile Strength, and Elongation Rate (ASTM D638):

Hardness, tensile strength, and elongation rate were measured in the same manner as described above.

Migration Resistance:

An initial weight (Wi) of each sample was measured to 4 decimal places. The sheet (3 cm×3 cm) was inserted between polystyrene plates in an 80° C. oven and maintained for 72 hours in the state of applying a load of 1 kg. Then, the sample was taken out from the oven and stored in a constant As illustrated in Table 2, it may be confirmed that physical properties of Examples 1 to 4 were the same as or better than those of Comparative Examples 1 and 2.

In particular, it may be confirmed that Examples 1 to 4 had a heating loss of about 1.4% to about 1.5%, but the heating loss of Comparative Example 1 was rapidly increased to 4.6%. That the heating loss rapidly increased as in Comparative Example 1 may denote that the amount of the ester-based plasticizer present in the sample was decreased by the increased amount.

With respect to the tensile strength, it may be understood that tensile strengths of Examples 1 to 4, in which the isophthalate and the terephthalate were mixed, were improved by 5% or more in comparison to that of Comparative Example 3 using only the isophthalate.

It may be understood that migration resistances of Examples 1 to 4 of the present invention were decreased by about 3% in comparison to that of Comparative Example 1, and heating losses of Examples 1 to 4 were decreased by 200% or more in comparison to that of Comparative Example 1.

<Physical Property Measurement According to Carbon Number>

In order to compare physical properties according to carbon numbers of the end groups of the isophthalate and the terephthalate, physical properties were measured under different conditions as in Table 3. In this case, the isophthalate and the terephthalate in the plasticizer were used at a weight ratio of 60:40 and a sheet was prepared by the same method as the above-described method of preparing a sheet. The isophthalate and the terephthalate in Examples 5 to 10 were respectively dialkyl isophthalate and diakyl terephthalate.

TABLE 3

| | Comparative Example 4 | Example 5 | Example 6 | Example 7 | Example 8 | Example 9 | Example 10 |
|---|---|---|---|---|---|---|---|
| Carbon number | P: C6 TP: C4 | IP: C8 TP: C8 | IP: C9 TP: C9 | IP: C10 TP: C10 | IP: C7 TP: C7 | IP: C6 TP: C6 | IP: C5 TP: C5 |
| One pot/Blending | (blending) | (one pot) | (one pot) | (one pot) | (one pot) | (one pot) | (one pot) |
| Physical properties — Hardness | 88.0 | 88.3 | 90.4 | 91.8 | 86.7 | 85.2 | 82.1 |
| Tensile strength (kg/cm$^2$) | 185.0 | 184.2 | 180.5 | 173.6 | 201.7 | 235.6 | 259.2 |
| Elongation rate (%) | 258.7 | 260.2 | 235.6 | 210.8 | 268.5 | 278.9 | 295.3 |
| Migration resistance (%) | 9.9 | 9.6 | 1.05 | 0.07 | 10.5 | 13.8 | 15.9 |
| Heating loss (%) | 3.5 | 1.3 | 0.68 | 0.50 | 12.3 | 15.6 | 24.3 |

IP: isophthalate
P: phthal-type ester
TP: terephthalate

As illustrated in Table 3, with respect to Examples 5 to 10 of the present invention, stable physical properties may be secured. In particular, with respect to Examples 5 to 7 in which the end groups of the isophthalate and the terephthalate had 8 to 10 carbon atoms, it may be understood that migration resistances and heating losses were significantly decreased by 10 times or more in comparison to those of Examples 8 to 10 using the esters having 7 or less carbon atoms.

Also, in the case that the isophthalate and the terephthalate were mixed, it may be understood that the heating loss was improved by about 3 times or more and the migration resistance was decreased by 9 times in comparison to Example 4 in which the terephthalate and the phthal-type ester were mixed.

Thus, the plasticizer of the present invention including the isophthalate and the terephthalate showed significant improvements in terms of migration resistance and heating loss as well as environmental friendliness in comparison to the plasticizer in which the terephthalate and DOP were mixed.

Furthermore, in the plasticizer of the present invention including the isophthalate and the terephthalate, it may be understood that physical properties of the plasticizer including the end group of the ester having 8 to 10 carbon atoms were significantly improved in comparison to those of the plasticizer including the end group of the ester having less than 8 carbon atoms.

<Physical Property Measurement According to Mixing Ratio of Isophthalate to Terephthalate>

In order to compare physical properties according to a mixing ratio of the isophthalate to the terephthalate, the isophthalate and the terephthalate were used at a weight ratio of 90:10, 80:20, 70:30, 60:40, 40:60, and 0:100, and physical properties were measured by preparing sheets by the same method as the above-described method of preparing a sheet. The results thereof are presented in Table 4.

TABLE 4

| | Example 11 | Example 12 | Example 13 | Example 14 | Example 15 | Comparative Example 5 |
|---|---|---|---|---|---|---|
| IP:TP (weight ratio) | 90:10 | 80:20 | 70:30 | 60:40 | 40:60 | 0:100 |
| Physical properties — Hardness | 88.0 | 88.2 | 88.5 | 88.5 | 89.5 | 91.5 |
| Elongation rate (%) | 261.3 | 259.4 | 257.9 | 258.8 | 256.5 | 252.1 |
| Migration resistance (%) | 10.0 | 9.9 | 9.9 | 9.8 | 9.7 | 9.4 |
| Heating loss (%) | 1.5 | 1.4 | 1.4 | 1.4 | 1.4 | 1.3 |

As illustrated in Table 4, in the case that the isophthalate and the terephthalate were used at a weight ratio of 90:10, 80:20, 70:30, 60:40, and 40:60 as in Examples 11 to 15 of the present invention, hardness was significantly improved in comparison to that of Comparative Example 5 using only the terephthalate.

In addition, the hardness was affected by the mixing ratio of the isophthalate to the terephthalate. That is, with respect to Examples 11 to 14 in which the amount of the isophthalate was greater than the amount of the terephthalate, the hardness was significantly reduced in comparison to that of Example 15 and Comparative Example 5 in which the amount of the terephthalate was greater than the amount of the isophthalate. The decrease in the hardness was effective in improving the productivity of the product, and it may be understood that the effect of increasing platicization efficiency was obtained due to excellent workability.

Also, the migration resistances and heating losses of Examples 11 to 15 were the same level as those of Comparative Example 5 and it was observed that the elongation rates were increased.

The plasticizer of the present invention including the isophthalate and the terephthalate had the same level of migration resistance and heating loss and increased hardness and elongation rate, and thus, the plasticizer of the present invention may improve the productivity and processability of the product.

The invention claimed is:

1. A plasticizer comprising isophthalate and terephthalate, wherein a weight ratio of the isophthalate to the terephthalate is in a range of 50:50 to 99:1.

2. The plasticizer of claim 1, wherein the isophthalate has an end group independently selected from alkyl groups having 1 to 12 carbon atoms.

3. The plasticizer of claim 2, wherein the isophthalate has an end group independently selected from alkyl groups having 8 to 10 carbon atoms.

4. The plasticizer of claim 2, wherein the isophthalate is dialkylisophthalate.

5. The plasticizer of claim 4, wherein the isophthalate has a structure represented by Chemical Formula 1:

[Chemical Formula 1]

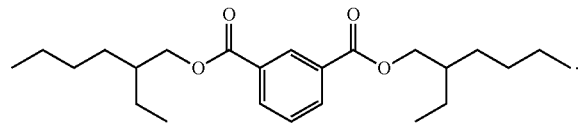

6. The plasticizer of claim 1, wherein the terephthalate has an end group independently selected from alkyl groups having 1 to 12 carbon atoms.

7. The plasticizer of claim 6, wherein the terephthalate has an end group independently selected from alkyl groups having 8 to 10 carbon atoms.

8. The plasticizer of claim 6, wherein the terephthalate is dialkylterephthalate.

9. The plasticizer of claim 8, wherein the terephthalate has a structure represented by Chemical Formula 2:

[Chemical Formula 2]

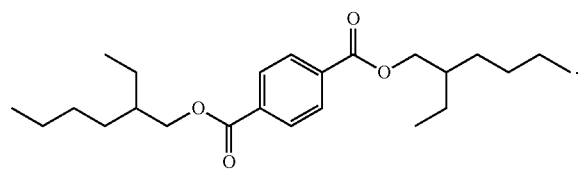

10. The plasticizer of claim 1, wherein the plasticizer is an ether-free plasticizer.

11. A method of preparing the plasticizer of claim 1, the method comprising steps of:
adding both isophthalic acid and terephthalic acid to alcohol to obtain a mixture, wherein the isophthalic acid and the terephthalic acid are mixed in a weight ratio of 50:50 to 99:1;
adding a catalyst to the mixture to react in a nitrogen atmosphere;
removing unreacted alcohol and neutralizing unreacted acid; and
dehydrating and filtering by vacuum distillation to obtain the plasticizer.

12. The method of claim 11, wherein the alcohol has an alkyl group having 1 to 12 carbon atoms.

13. The method of claim 11, wherein the alcohol is used in an amount of 150 mol % to 500 mol % based on 100 mol % of the isophthalic acid.

14. A method of preparing the plasticizer of claim 1, the method comprising:
preparing an ester-based mixture including terephthalate and isophthalate; and
obtaining the plasticizer by blending the terephthalate and the isophthalate to include the isophthalate in an amount of 50 wt % to 99 wt % based on a total weight of the ester-based mixture.

15. A resin composition comprising the plasticizer of claim 1 in an amount of 5 parts by weight to 150 parts by weight based on 100 parts by weight of a resin selected from the group consisting of ethylene vinyl acetate, polyethylene, polypropylene, polyvinyl chloride, polystyrene, polyurethane, and a thermoplastic elastomer.

16. The resin composition of claim 15, wherein the composition is used in a compound formulation or a sheet formulation.

17. The resin composition of claim 15, wherein the composition is used in manufacturing electric wires, flooring materials, automotive interior materials, films, sheets, wallpaper, or tubes.

* * * * *